US00PP22014P3

(12) United States Plant Patent
Loch

(10) Patent No.: US PP22,014 P3
(45) Date of Patent: Jul. 5, 2011

(54) ZOYSIAGRASS PLANT 'A-1'

(50) Latin Name: *Zoysia matrella*
Varietal Denomination: A-1

(75) Inventor: Donald S. Loch, Alexandra Hills (AU)

(73) Assignee: Genegro Pty Ltd, Alexandra Hills (AU)

( * ) Notice: Subject to any disclaimer, the term of this patent is extended or adjusted under 35 U.S.C. 154(b) by 0 days.

(21) Appl. No.: 12/453,550

(22) Filed: May 14, 2009

(65) Prior Publication Data

US 2010/0293688 P1 Nov. 18, 2010

(51) Int. Cl.
*A01H 5/00* (2006.01)

(52) U.S. Cl. ..... Plt./390

(58) Field of Classification Search ..... Plt./390
See application file for complete search history.

(56) References Cited

U.S. PATENT DOCUMENTS

PP10,636 P 10/1998 Engelke
PP10,778 P 2/1999 Engelke
PP14,130 P2 9/2003 Engelke et al.
PP14,395 P2 12/2003 Engelke et al.

OTHER PUBLICATIONS

Australian Government: IP Australia, Plant Varieties Journal, vol. 21, No. 1, Jun. 6, 2008, Application No. 2008/091.

*Primary Examiner* — Kent L Bell
(74) *Attorney, Agent, or Firm* — Hunton & Williams LLP

(57) ABSTRACT

An asexually reproduced cultivar of perennial zoysiagrass that possesses a unique combination of characteristics including high turf quality and density under mowing, good shade tolerance, salinity tolerance, resistance to *zoysia* rust and Rhizoctonia blight, moderate to good resistance to tropical sod webworm and armyworm, and a distinctive DNA profile.

6 Drawing Sheets

Botanical classification: *Zoysia matrella.*
Variety denomination: 'A-1'.

BACKGROUND OF THE INVENTION

1. Field of the Invention

The present invention relates to a new and distinct asexually reproduced perennial zoysiagrass cultivar named 'A-1'.

2. Description of Prior Art

Zoysiagrasses are a widely used group of warm-season turfgrasses in the southern United States. The group includes three species and their interspecific hybrids: *Zoysia japonica* Steud., *Z. matrella* (L.) Merr., and (rarely) *Zoysia pacifica* (Goudswaard) Hotta & Kuroki (formerly assigned to *Z. tenuifolia* Thiele). All are rhizomatous and stoloniferous, mat-forming perennials adapted to a wide range of edaphic conditions.

Compared with other warm-season turfgrasses such as Bermudagrasses and St. Augustinegrass, zoysiagrasses are very resistant to wear damage, but slow to spread laterally by stolons and rhizomes and are therefore slower to recover from wear damage. *Z. japonica* produces coarse to medium-textured leaves and is adapted from subtropical to cool temperate conditions, while *Z. matrella* produces medium to fine-textured leaves and is adapted to warmer climates from tropical through to warm temperate.

Prior art *Z. matrella* and *Z. matrella*×*Z. japonica* zoysiagrasses include 'Diamond' (U.S. Plant Pat. No. 10,636), 'Cavalier' (U.S. Plant Pat. No. 10,778), 'Zorro' (U.S. Plant Pat. No. 14,130), and 'Royal' (U.S. Plant Pat. No. 14,395).

BRIEF SUMMARY OF THE INVENTION

The present invention relates to a new and distinct perennial *Zoysia matrella* zoysiagrass cultivar identified as 'A-1'.

'A-1' differs from other known *Z. matrella* and *Z. matrella*×*Z. japonica* cultivars with respect to a number of morphological characteristics, shows greater winter hardiness, and has a distinctive DNA profile. 'A-1' produces shorter, narrower leaves (i.e., finer-textured foliage), shorter, erect tillers, and larger inflorescences on longer, thinner peduncles than 'Cavalier' and 'Zorro'. Compared with 'Royal', 'A-1' has narrower leaves, but produces larger inflorescences on longer, thinner peduncles. 'A-1' produces longer stolon internodes, longer vertical tillers with more elongated leaves (i.e., greater length:width ratio), and larger inflorescences on longer, thicker peduncles than 'Diamond'. 'A-1' also has good shade and salinity tolerance, is tolerant of zoysia rust and resistant to Rhizoctonia blight, and shows moderate to good resistance to tropical sod webworm and armyworm.

The electropherograms (from the top panel to the bottom panel) are from 'Royal', 'Zorro', 'Cavalier', 'A-1' and 'Diamond'.

DETAILED DESCRIPTION OF THE INVENTION

'A-1' was selected from a breeding population of forty *Zoysia matrella* plants derived from open-pollinated seed collected from various parts of Southeast Asia (Japan, Philippines, China, Korea, Vietnam and Thailand). The original plants were vegetatively propagated and evaluated first in pots at Sheldon, QLD (Australia). Vegetative propagation was performed by using stolons from the original plant and dividing them into stolon tip and single-node cuttings. These cuttings were placed into soilless peat-vermiculite potting mix in nursery cell trays to produce roots and grow through the potting medium before transplanting into larger pots.

A shortlist of selected genotypes was expanded to field plantings at Sheldon, QLD (Australia). The plants were vegetatively propagated in nursery cell trays prior to planting in the field. Once in the field, the plants were evaluated against existing *Z. matrella* and *Z. matrella*×*Z. japonica* hybrid cultivars under mowing heights from 10 to 25mm and under shade levels ranging from 0 to 80%. 'A-1' from seed collected in northern Okinawa (Japan) showed higher tiller density and a more prostrate growth habit than the parent ecotypes which formed a more open sward and were more erect in their growth habit. 'A-1' was selected from the wider breeding population on the basis of its superior turf colour, quality under mowing for 6 years, and its shade tolerance as shown by its ability to maintain density of the mown sward under greatly reduced light levels (70-80% shade). Additional observations regarding climatic adaptation were made in Cairns, QLD (Australia) and Melbourne, VIC (Australia) using vegetative propagules as described above. 'A-1' has remained true-to-type with no discernible off-types through more than four cycles of vegetative multiplication.

DETAILED BOTANICAL DESCRIPTION

'A-1' is a perennial diploid (2n=40 chromosomes) *Zoysia matrella* (L) Merr. zoysiagrass with a creeping growth habit forming a tight mat of stolons rooting adventitiously on the ground surface. It spreads laterally by stolons and rhizomes, which produce very short vertical tillers (<10 cm tall) with fine stems (<0.6 mm diameter).

Figure 2A:
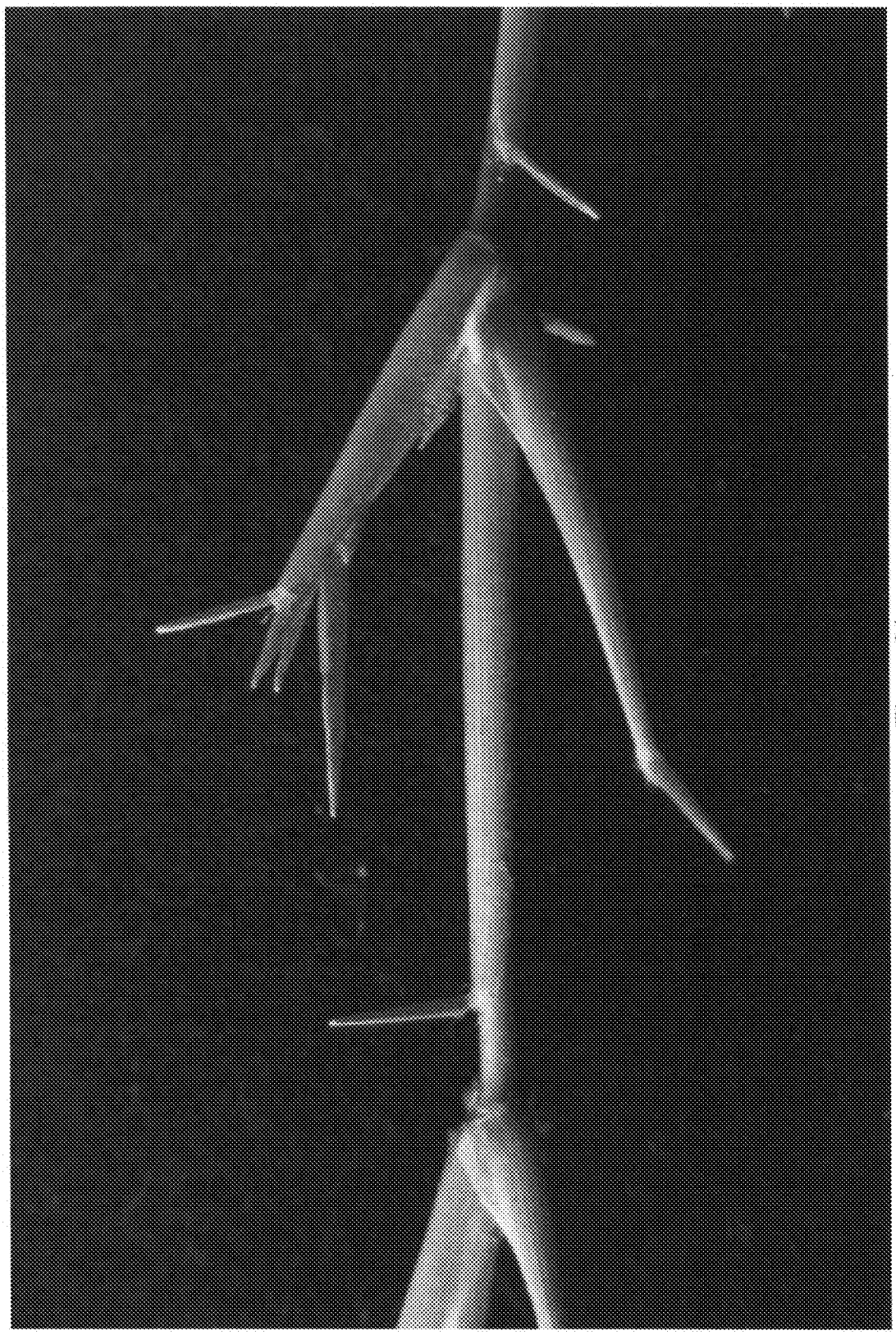
FIGS. 2A-2C are photographs of compound stolon nodes from 'A-1' showing a compressed node subtended by 3 stolon leaves (FIG. 2A), the progressive development of branching at nodes along a stolon (FIG. 2B), and complex branching from older compound nodes (FIG. 2C). Vestigal leaf blades are present on the stolon leaves.
Figure 2B:
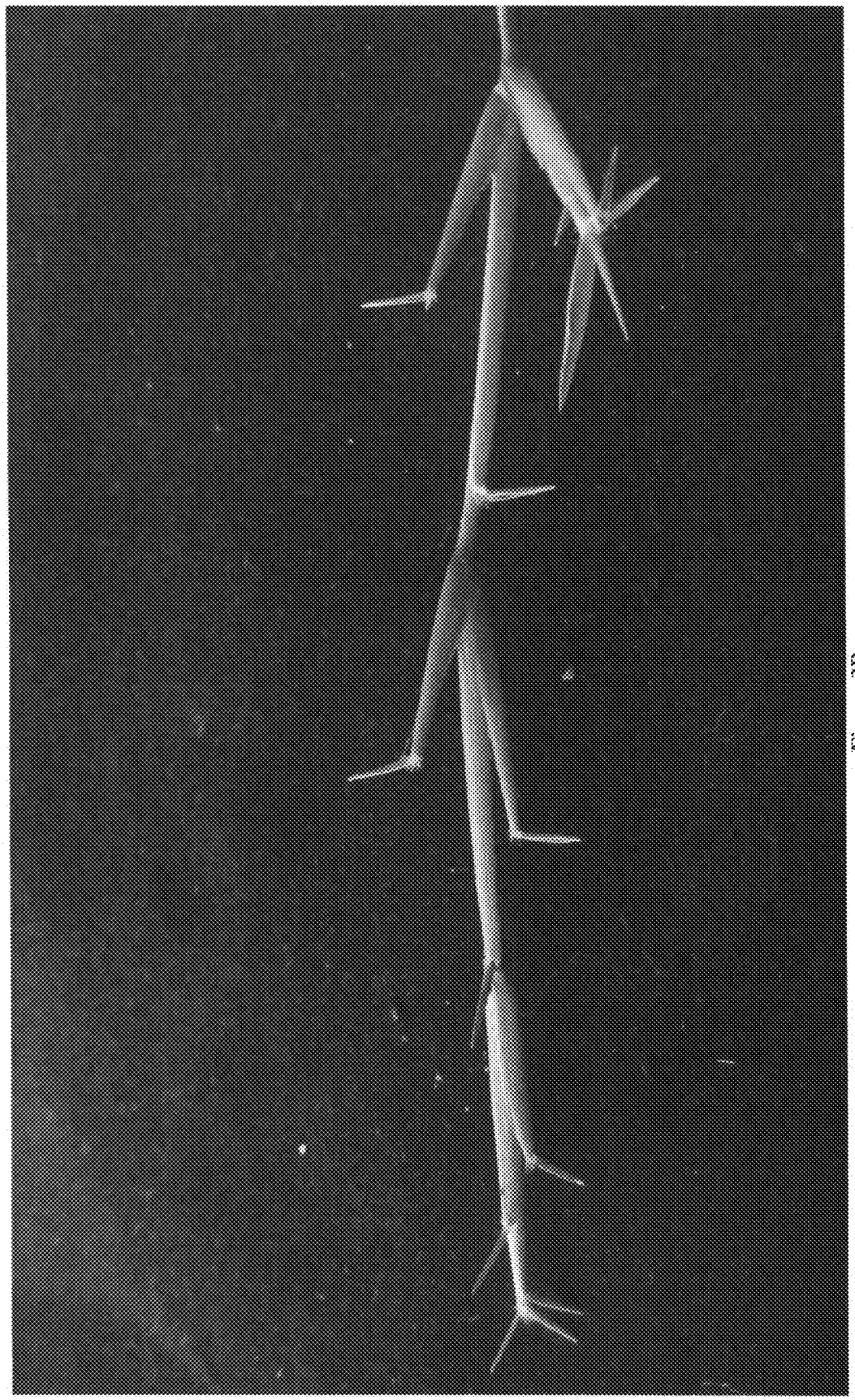
Figure 2C:
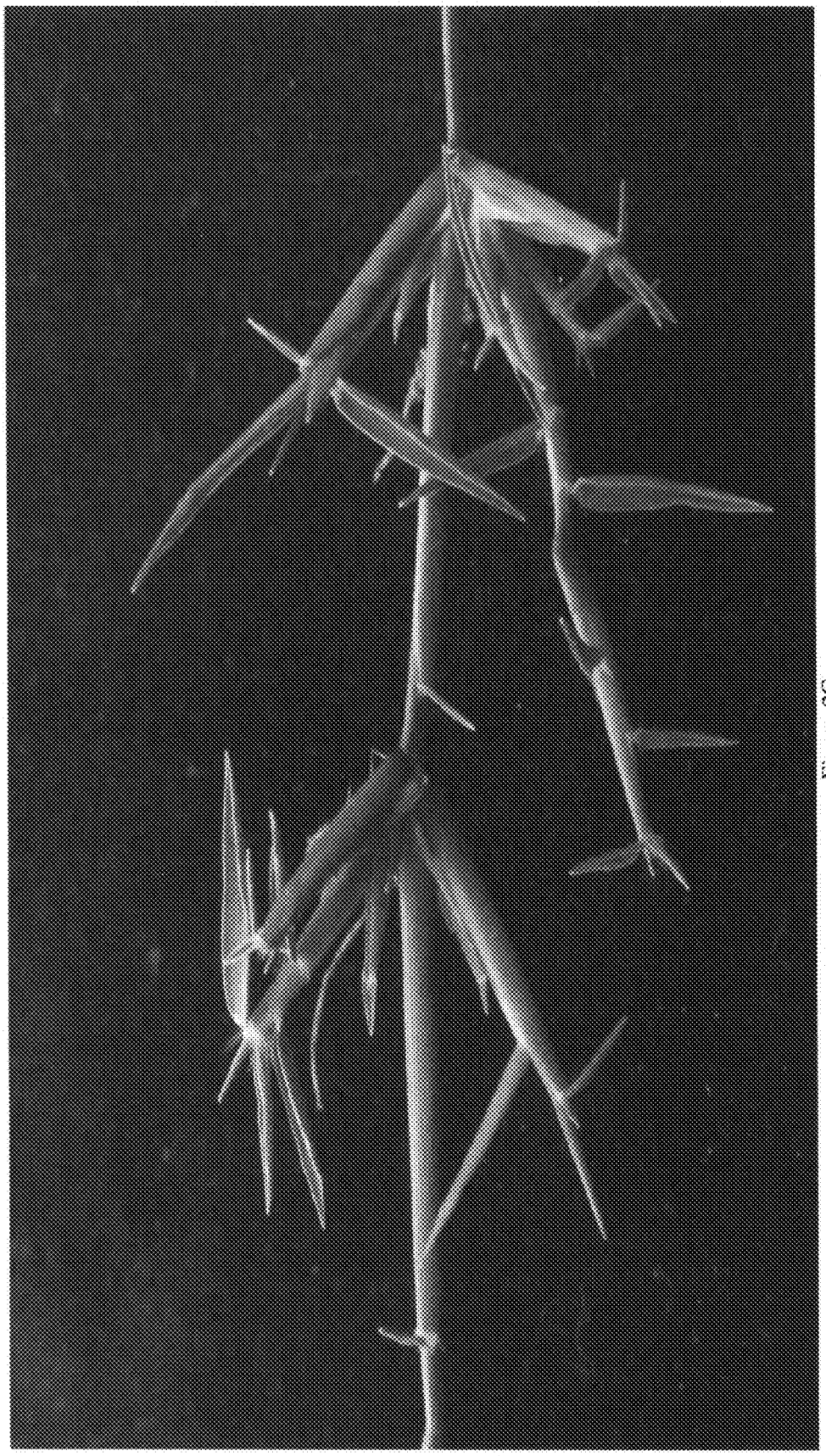

The stolons of 'A-1' consist of short, thin internodes separated by compound nodes, each of which is subtended by 3 leaves (FIG. 2). Structurally, each compound node consists of two compressed internodes and one normal internode and so can produce axillary stolon shoots (i.e., branches) from any or all of the three component nodes, starting from the component node furthest from the stolon tip and subtended by the outermost stolon leaf (FIG. 2).

Internodes on 'A-1' are longer than on 'Diamond', but comparable in length to those of 'Cavalier', 'Zorro' and 'Royal'. 'A-1' produces fewer early stolon shoots per node than 'Diamond', 'Cavalier' and 'Zorro'. Stolon color is reddish-purple (RHS N79A—RHS Colour Chart, 2001 edition) when exposed to sunlight. Stolon leaf blades are linear-triangular in shape and greatly reduced (vestigal) compared with tiller leaves. Stolon leaf blades on 'A-1' are longer and wider (i.e., better developed) than those of 'Cavalier' 'Zorro', 'Royal' and 'Diamond'.

Measurements relating to 'A-1' internodes and stolons are described in Table 1 and as follows:

*Mean length of* 4*th internode from stolon tip.*—23.04 mm.

*Mean diameter of* 4*th internode from stolon tip.*—1.37 mm.

*Mean length:diameter ratio of* 4th internode from stolon tip.—16.76.

*Mean number of axillary shoots at* 4th visible stolon node.—2.30.

*Mean length of outermost leaf sheath on* 4th visible node from stolon tip.—9.61 mm.

*Mean length of innermost leaf sheath on* 4th visible node from stolon tip.—20.05 mm.

*Mean length of leaf blades on* 4th visible node from stolon tip.—4.23 mm.

*Mean width of leaf blades on* 4th visible node from stolon tip.—0.85 mm.

*Mean length:width ratio of leaf blades on* 4th visible node from stolon tip.—5.04.

Tiller length (i.e., vertical extension) on 'A-1' is shorter than 'Cavalier' and 'Zorro', but longer than 'Diamond'. Leaf blades are rolled in the bud and later emerge to become flat and stiff, linear-triangular in shape with smooth margins and a sharply acute apex. 'A-1' produces shorter, narrower leaf blades than 'Cavalier' and 'Zorro'. Hairs are absent on both the abaxial and adaxial surfaces of the leaf blade and on the leaf sheath. Leaf blade color is dark green (RHS 137A—R.H.S. Colour Chart, 2001 edition). The tiller stem and leaf sheath are mid-green (RHS 138B—R.H.S. Colour Chart, 2001 edition). The ciliate ligule consists of a row of short silky white (RHS N155A—R.H.S. Colour Chart, 2001 edition) hairs up to 4 mm long.

Measurements relating to 'A-1' tillers are described in Table 1 and as follows:

*Mean length of flag leaf sheath on flowering tillers.*—22.73 mm.

*Mean length of flag leaf blade on flowering tillers.*—3.90 mm.

*Mean width of flag leaf blade on flowering tillers.*—0.71 mm.

*Mean length:width ratio of flag leaf blade on flowering tillers.*—5.49.

*Mean length of sheath on fourth leaf on flowering tillers.*—10.22 mm.

*Mean length of blade on fourth leaf on flowering tillers.*—17.98 mm.

*Mean width of blade on fourth leaf on flowering tillers.*—1.61 mm.

*Mean length:width ratio of blade on fourth leaf on flowering tillers.*—11.12.

'A-1' flowers from about April to October in the southern hemisphere, and October to April in the northern hemisphere. The inflorescence is a short, terminal, spike-like raceme 12-24 mm long, 1.2-1.6 mm in diameter, and dark greyed-orange in colour (RHS 166A—R.H.S. Colour Chart, 2001 edition) while immature. The peduncle below the inflorescence is mid-green (RHS 138B—R.H.S. Colour Chart, 2001 edition) in color. 'A-1' produces longer peduncles and racemes and has more spikelets per inflorescence than 'Cavalier', 'Zorro', 'Royal', and 'Diamond'; the density of spikelets on the raceme (number per mm of length) is also significantly higher than for 'Cavalier', 'Zorro', 'Royal' and 'Diamond'. Peduncles on 'A-1' are thinner than those on 'Cavalier', 'Zorro', and 'Royal', but thicker than 'Diamond' peduncles. Mature spikelets are glabrous, pale greyed-yellow in colour (RHS 161C—R.H.S. Colour Chart, 2001 edition), narrowly ovoid (2.5-3.0 mm long X 0.8-1.0 mm wide) in shape with the upper glume tapering to an acute apex minutely bilobed and tipped with a short mucronate awn to c. 1.0 mm long.

Measurements relating to 'A-1' peduncles, racemes, and spikelets are described in Table 1 and as follows:

*Mean length of peduncle.*—41.54 mm.

*Mean width of peduncle.*—0.56 mm.

*Mean raceme length.*—17.94 mm.

*Mean number of spikelets per inflorescence.*—23.5.

*Mean number of spikelets per mm of raceme length.*—1.31.

'A-1' was compared against other *Zoysia matrella* and *Z. matrella×Z. japonica* cultivars 'Diamond', 'Cavalier', 'Royal', and 'Zorro' in a spaced-plant field trial at Cleveland, QLD (Australia) (Latitude 27° 32'S, 153° 15'E, elevation c. 50 masl). Morphological grouping characteristics used to select the most similar comparator varieties of common knowledge were stolon internode length, leaf blade length and width, leaf length and width on flowering tillers, peduncle length and width, and inflorescence length (Table 1).

Figure 1:
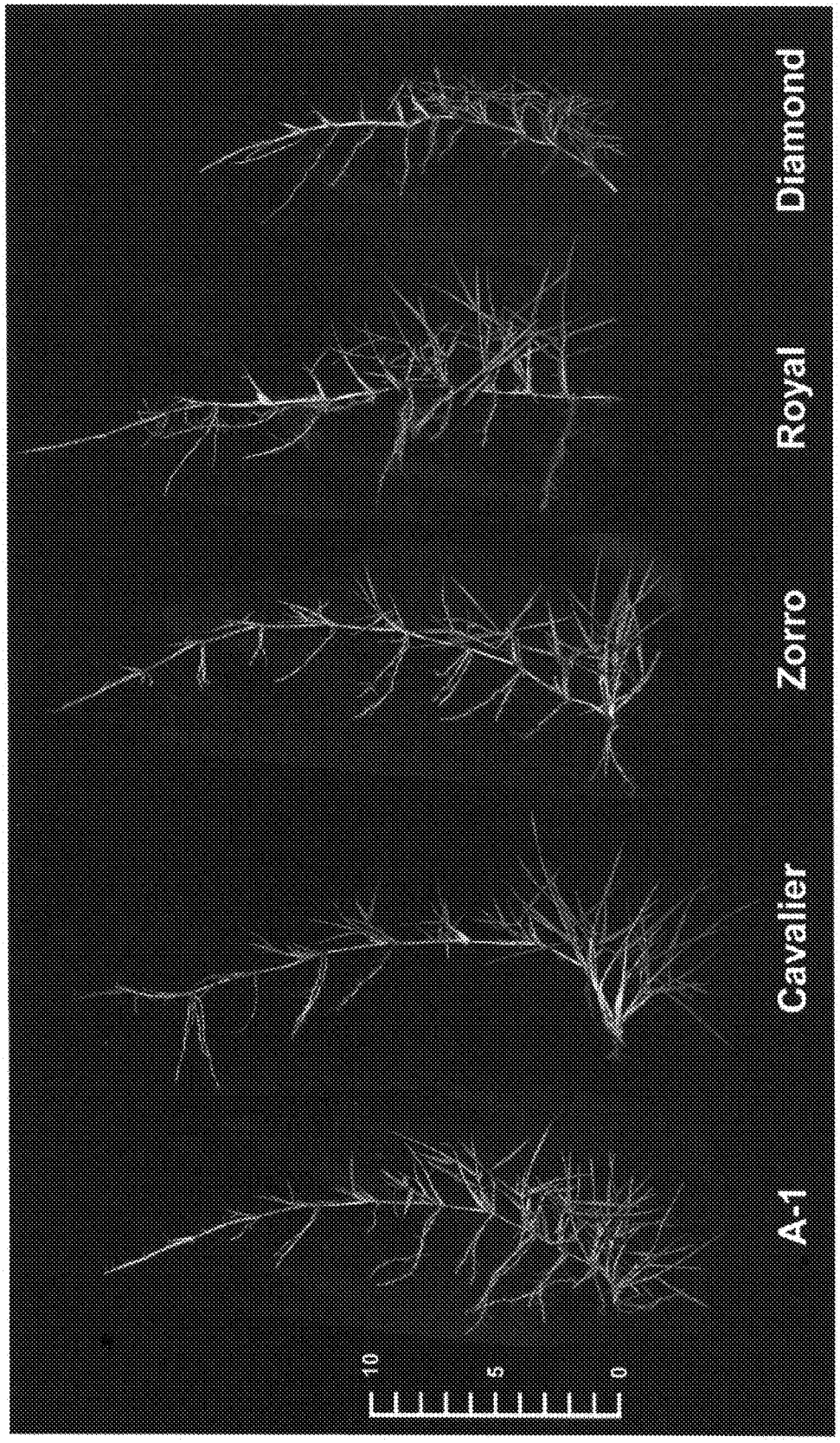
FIG. 1 is a photograph showing stolon comparisons of five *Zoysia matrella* and *Z. matrella*×*Z. japonica* cultivars: 'A-1', 'Cavalier', 'Zorro', 'Royal', and 'Diamond'.

Rooted vegetative plugs 5 cm in diameter were taken from nursery stock and planted on a basaltic red ferrosol soil on March 3, 2003 on a 1m×1m grid. Thirty spaced plants from each of the five cultivars were arranged in three randomized blocks with ten plants per plot. Weed control was achieved by a pre-emergence application of oxadiazon (repeated on Jul. 23, 2003) and with post-emergence fluroxypyr for broadleaf weeds on Mar. 23, 2003. Good nutrition was maintained by regular applications of slow release complete NPK fertilizer at one- to two-month intervals. The spaced plants were allowed to grow and develop without any mowing. Leaf and stolon colors were determined on Jul. 16, 2003. Diameter of spread was taken from four measurements per plant made on Aug. 22, 2003. Shoot and inflorescence characteristics were measured on two mature tillers between September 17 and 19, 2003. Stolon stem and leaf characteristics were measured on two stolons per plant between Oct. 6 and 10, 2003. Digital images of stolon characteristics (FIG. 1) were taken Dec. 10, 2003.

TABLE 1

Morphological/Agronomic Data from Comparative Growing Trial. Numerical data entries show the mean value of 60 measurements from each variety, with the standard deviation shown below the mean in parentheses.

| Attribute | 'A-1' | 'Cavalier' | 'Zorro' |
|---|---|---|---|
| Mean plant diameter after 173 days (cm) | 55.9 (9.4) | 82.6 (12.9) | 74.0 (16.1) |
| Number of axillary shoots at 4th visible stolon node (spaced plants) | 2.30 (0.59) | 3.18 (0.79) | 3.05 (0.81) |
| Length of 4th internode from stolon tip (mm) | 23.0 (4.64) | 24.6 (5.48) | 26.1 (6.05) |
| Diameter of 4th internode from stolon tip (mm) | 1.37 (0.15) | 1.39 (0.15) | 1.36 (0.19) |
| Length:diameter ratio of 4th internode from stolon tip | 16.76 (0.15) | 17.69 (0.15) | 19.03 (0.19) |
| Length of outermost leaf sheath on 4th visible node from stolon tip (mm) | 9.61 (1.91) | 8.88 (1.68) | 9.31 (2.49) |
| Length of innermost leaf sheath on 4th visible node from stolon tip (mm) | 20.05 (3.04) | 18.11 (3.23) | 17.42 (4.19) |
| Length of leaf blades on 4th visible node from stolon tip (mm) | 4.23 (0.79) | 3.02 (0.74) | 2.95 (0.84) |
| Width of leaf blades on 4th visible node from stolon tip (mm) | 0.85 (0.14) | 0.73 (0.14) | 0.70 (0.13) |
| Length:width ratio of leaf blades on fourth visible node from stolon tip | 5.04 (0.59) | 4.18 (0.70) | 4.22 (0.73) |

TABLE 1-continued

Morphological/Agronomic Data from Comparative Growing Trial. Numerical data entries show the mean value of 60 measurements from each variety, with the standard deviation shown below the mean in parentheses.

| | | | |
|---|---|---|---|
| Length of flag leaf sheath on flowering tillers (mm) | 22.73 (4.67) | 19.70 (2.27) | 20.38 (2.62) |
| Length of flag leaf blade on flowering tillers (mm) | 3.90 (1.97) | 3.61 (1.21) | 3.80 (0.99) |
| Width of flag leaf blade on flowering tillers (mm) | 0.71 (0.26) | 0.82 (0.22) | 0.67 (0.15) |
| Length:width ratio of flag leaf blade on flowering tillers | 5.49 (2.07) | 4.45 (1.02) | 5.75 (1.10) |
| Length of sheath on fourth leaf on flowering tillers (mm) | 10.22 (2.55) | 14.10 (3.52) | 16.07 (3.31) |
| Length of blade on fourth leaf on flowering tillers (mm) | 17.98 (6.05) | 29.16 (8.99) | 32.58 (8.88) |
| Width of blade on fourth leaf on flowering tillers (mm) | 1.61 (0.40) | 1.93 (0.32) | 2.01 (0.26) |
| Length:width ratio of fourth leaf blade on flowering tillers | 11.12 (2.47) | 15.04 (3.63) | 16.16 (3.92) |
| Length of peduncle (mm) | 41.54 (11.78) | 34.92 (6.35) | 35.10 (6.41) |
| Diameter of peduncle (mm) | 0.56 (0.10) | 0.72 (0.10) | 0.70 (0.09) |
| Mean raceme length (mm) | 17.94 (2.52) | 15.05 (1.48) | 14.73 (1.73) |
| Number of spikelets per inflorescence | 23.5 (3.7) | 18.0 (4.0) | 17.3 (3.9) |
| Number of spikelets per mm of raceme length | 0.78 (0.12) | 0.88 (0.25) | 0.90 (0.24) |
| Color of stolon stem exposed to sunlight (RHS Colour Chart, 2001 edition) | N79A | N79A | N79A |
| Color of leaf blade (RHS Colour Chart, 2001 edition) | 137A | 137A | 137C |

| Attribute | 'Royal' | Diamond' | LSD (P = 0.05) |
|---|---|---|---|
| Mean plant diameter after 173 days (cm) | 62.2 (13.1) | 37.5 (7.2) | 12.9 |
| Number of axillary shoots at 4th visible stolon node (spaced plants) | 2.83 (0.83) | 4.13 (1.19) | 0.51 |
| Length of 4th internode from stolon tip (mm) | 22.2 (3.56) | 11.1 (2.28) | 3.9 |
| Diameter of 4th internode from stolon tip (mm) | 1.44 (0.11) | 1.36 (0.18) | 0.11 |
| Length:diameter ratio of 4th internode from stolon tip | 15.45 (0.11) | 8.20 (0.18) | 1.43 |
| Length of outermost leaf sheath on 4th visible node from stolon tip (mm) | 10.33 (1.41) | 7.33 (1.54) | 1.31 |
| Length of innermost leaf sheath on 4th visible node from stolon tip (mm) | 19.11 (3.05) | 13.45 (2.72) | 2.71 |
| Length of leaf blades on 4th visible node from stolon tip (mm) | 2.55 (0.47) | 1.53 (0.35) | 0.47 |
| Width of leaf blades on 4th visible node from stolon tip (mm) | 0.62 (0.11) | 0.50 (0.10) | 0.10 |
| Length:width ratio of leaf blades on fourth visible node from stolon tip | 4.18 (0.73) | 3.13 (0.59) | 0.54 |
| Length of flag leaf sheath on flowering tillers (mm) | 19.57 (3.57) | 13.99 (1.55) | 2.26 |
| Length of flag leaf blade on flowering tillers (mm) | 3.21 (1.05) | 3.35 (1.21) | 0.66 |
| Width of flag leaf blade on flowering tillers (mm) | 0.68 (0.17) | 0.66 (24) | 0.16 |
| Length:width ratio of flag leaf blade on flowering tillers | 4.78 (1.24) | 5.18 (1.28) | 0.99 |
| Length of sheath on fourth leaf on flowering tillers (mm) | 12.55 (2.64) | 7.96 (1.23) | 1.30 |
| Length of blade on fourth leaf on flowering tillers (mm) | 21.05 (7.89) | 15.56 (2.99) | 3.86 |
| Width of blade on fourth leaf on flowering tillers (mm) | 1.66 (0.38) | 1.53 (0.25) | 0.27 |
| Length:width ratio of fourth leaf blade on flowering tillers | 12.83 (4.65) | 10.33 (2.15) | 1.03 |
| Length of peduncle (mm) | 32.31 (10.91) | 19.71 (3.57) | 5.80 |
| Diameter of peduncle (mm) | 0.65 | 0.43 | 0.05 |

TABLE 1-continued

Morphological/Agronomic Data from Comparative Growing Trial. Numerical data entries show the mean value of 60 measurements from each variety, with the standard deviation shown below the mean in parentheses.

| | | | |
|---|---|---|---|
| | (0.11) | (0.06) | |
| Mean raceme length (mm) | 14.92 | 10.68 | 0.91 |
| | (2.29) | (1.20) | |
| Number of spikelets per inflorescence | 16.3 | 9.0 | 1.8 |
| | (4.2) | (1.6) | |
| Number of spikelets per mm of raceme length | 1.03 | 1.21 | 0.14 |
| | (0.38) | (0.23) | |
| Color of stolon stem exposed to sunlight (RHS Colour Chart, 2001 edition) | N79A | N79A | |
| Color of leaf blade (RHS Colour Chart, 2001 edition) | 137A | 137A | |

STRESS RESISTANCE

'A-1' shows excellent salt tolerance. In a greenhouse experiment, six salinity levels covering the range from 60 to 25,600 ppm Total Dissolved Salts (TDS) applied as NaC1 were imposed hydroponically through the irrigation water. After being held at the designated treatment levels for thirteen weeks, the level of leaf firing induced in 'A-1' was comparable to that in 'Diamond', 'Cavalier', 'Zorro', and 'Royal' (Table 2). The relative dry matter yield of clippings over the ten- to fourteen-week period in 'A-1' was lower than 'Diamond' and 'Royal' at the highest salinity level (25,600 ppm TDS), but was superior to the other four cultivars at 5,120 ppm TDS and generally comparable to them at intermediate salinity levels (Table 3).

TABLE 2

Effect of salinity level on percent leaf firing of *Zoysia matrella* cultivars) after thirteen weeks of treatment. LSD (P = 0.05) = 10.3.

| | TDS (ppm) | | | | | |
|---|---|---|---|---|---|---|
| Cultivar | 60 | 5,120 | 10,240 | 15,360 | 20,480 | 25,600 |
| 'A-1' | 5.0 | 23.3 | 31.7 | 64.2 | 61.7 | 90.7 |
| 'Diamond' | 2.8 | 11.7 | 24.2 | 46.7 | 61.7 | 87.5 |
| 'Cavalier' | 4.5 | 30.8 | 40.0 | 69.2 | 72.5 | 94.7 |
| 'Zorro' | 6.7 | 22.5 | 45.8 | 72.5 | 71.7 | 91.7 |
| 'Royal' | 8.3 | 50.0 | 50.0 | 73.3 | 73.3 | 90.7 |

TABLE 3

Effect of salinity level on dried clipping yield of *Zoysia matrella* cultivars relative to the control treatment (=1.000) after fourteen weeks of treatment. LSD (P = 0.05) = 0.149.

| | TDS (ppm) | | | | | |
|---|---|---|---|---|---|---|
| Cultivar | 60 | 5,120 | 10,240 | 15,360 | 20,480 | 25,600 |
| 'A-1' | 1.000 | 1.073 | 0.773 | 0.448 | 0.270 | 0.081 |
| 'Diamond' | 1.000 | 0.680 | 0.604 | 0.427 | 0.449 | 0.307 |
| 'Cavalier' | 1.000 | 0.656 | 0.450 | 0.321 | 0.252 | 0.000 |
| 'Zorro' | 1.000 | 0.822 | 0.671 | 0.321 | 0.141 | 0.096 |
| 'Royal' | 1.000 | 0.716 | 0.833 | 0.462 | 0.326 | 0.238 |

'A-1' is tolerant of zoysia rust (*Puccinia zoysiae*) and is resistant to Rhizoctonia blight. It is also resistant to sod webworm (*Herpetogramma licarsisalis*) and armyworm (*Pseudaletia* spp., *Spodoptera* spp.), except where excessive nitrogen fertilizer use causes softer leaves.

'A-1' has shown superior drought and winter hardiness to 'Diamond', 'Cavalier', 'Zorro' and 'Royal' in a trial at South Oakleigh, VIC (Australia) (37° 55'S, 145° 06'E). In plots planted with rooted stolon cuttings in October 2004, 'A-1' grew in faster and maintained good ground cover and turf quality (ratings 4.0-7.0) over the following two summers relative to the other 4 cultivars. Following summer drought without irrigation, turf quality-cover ratings for 'Diamond', 'Cavalier', 'Zorro' and 'Royal' declined to 1.5-2.0 (compared with 4.0 for 'A-1') in March 2006, and did not recover over the 2006 winter. At the end of the trial in March 2007 (2½years after planting), turf quality-cover ratings for 'Diamond', 'Cavalier', 'Zorro' and 'Royal' remained very low (1.5-2.5) compared with 'A-1' (6.0).

TABLE 4

Turf quality-ground cover ratings (0 = worst; 9 = best) for 5 *Zoysia matrella* cultivars planted at South Oakleigh (VIC, Australia) in October 2004.

| Cultivar | September 2005 | December 2005 | March 2006 | June 2006 | September 2006 | December 2006 | March 2007 |
|---|---|---|---|---|---|---|---|
| 'A-1' | 5.5 | 7.0 | 4.0 | 4.5 | 5.0 | 6.0 | 6.0 |
| 'Diamond' | 4.0 | 5.0 | 1.5 | 0.5 | 0.5 | 1.0 | 2.0 |
| 'Cavalier' | 4.5 | 4.0 | 2.0 | 2.0 | 1.5 | 1.0 | 1.5 |
| 'Zorro' | 3.0 | 3.0 | 1.5 | 1.0 | 1.0 | 2.0 | 2.5 |
| 'Royal' | 4.8 | 3.0 | 2.0 | 1.0 | 1.5 | 1.0 | 2.0 |

DNA PROFILING

Figure 3:
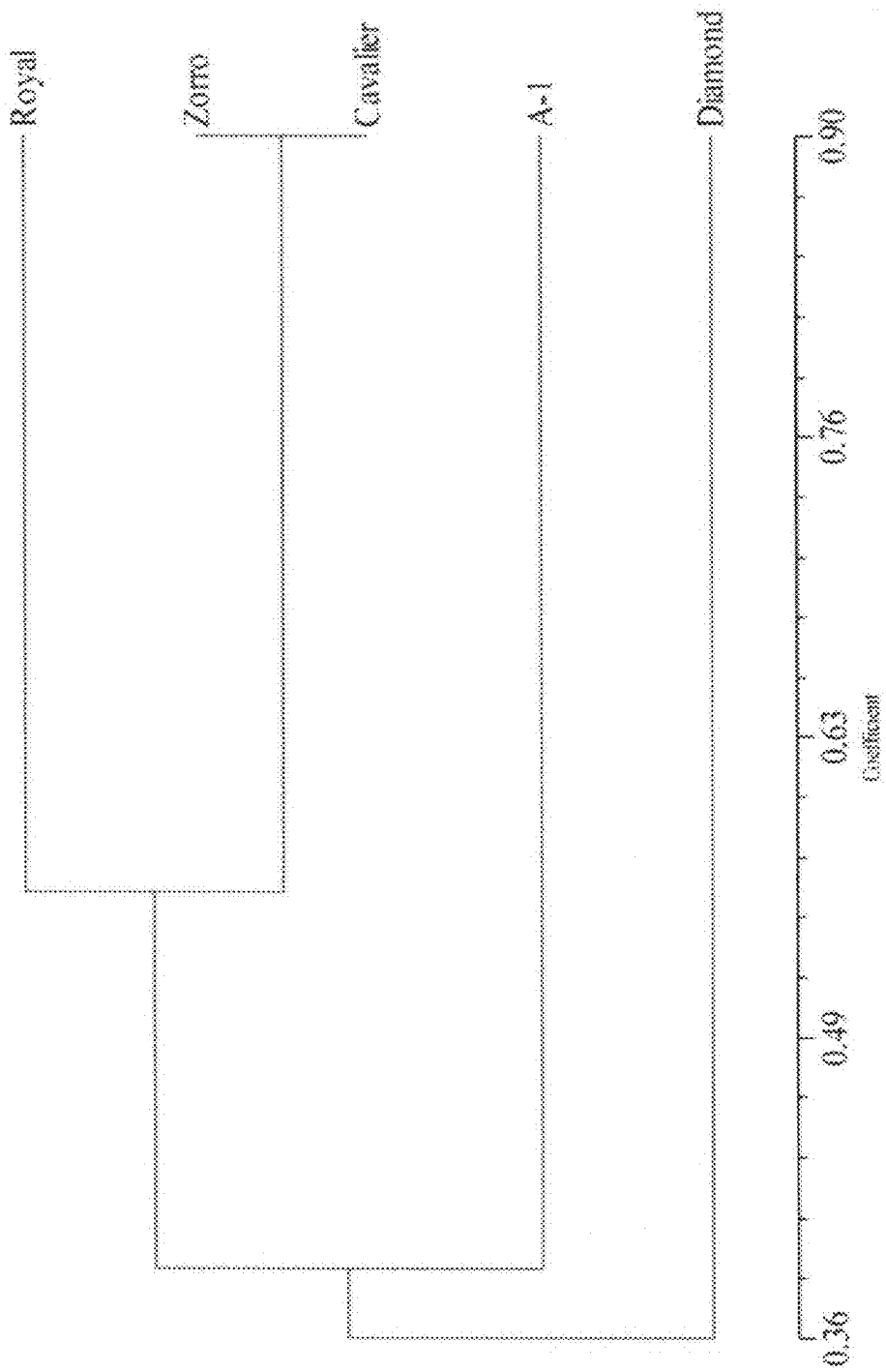
FIG. 3 shows the dendrogram for 'Royal', 'Zorro', 'Cavalier', 'A-1', and 'Diamond' constructed from 71 markers generated from two ISSR primers using Jaccard's coefficient.
Figure 4:
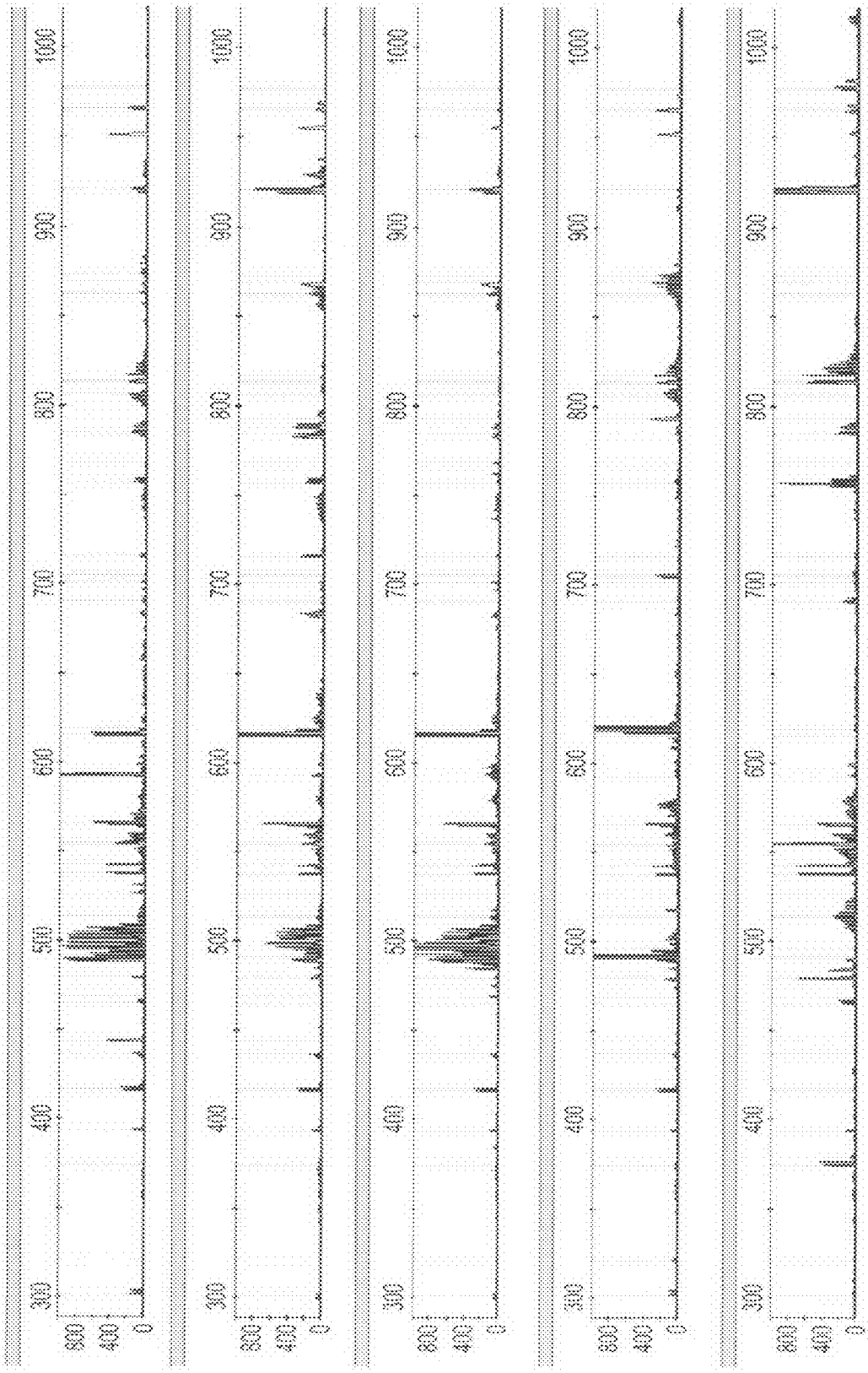
FIG. 4 presents the electropherogram for 'A-1' versus four other zoysiagrass genotypes using primer 6FAM $(AG)_9$,C.

DNA was extracted from ground leaf material using a modified CTAB (cetyl tri-methyl ammonium bromide) procedure. Inter-Simple-Sequence-Repeat (ISSR) markers were generated by the polymerase chain reaction (PCR) using a GeneWorks thermal cycler and two fluorescently labelled primers, 6FAM $(AG)_9C$ and NED $(GA)_9T$. Amplification products were separated by capillary electrophoresis using an ABI 3130 genotyper and visualised using GENEMAPPER® software. The dominant markers generated with both primers were then used to produce a dendrogram (FIG. 3) using pattern analysis. Distinctive marker loci were identified by both primers. FIG. 4, as an example, illustrates the distinctive marker loci identified using primer 6FAM $(AG)_9C$.

What is claimed is:

1. A new and distinct cultivar of *Zoysia matrella* Merr. plant named 'A-1' as described and illustrated herein.

* * * * *